United States Patent [19]
Comyn et al.

[11] Patent Number: 5,439,172
[45] Date of Patent: Aug. 8, 1995

[54] PLANAR SAMPLER FOR A LIQUID VOLATILE MATERIAL AND METHOD

[75] Inventors: John Comyn, Huncote; Derek A. Bishopp, Saxmundham, both of Great Britain

[73] Assignee: The Beautiful Bouquet Company Limited, England

[21] Appl. No.: 156,578

[22] Filed: Nov. 23, 1993

[30] Foreign Application Priority Data

Nov. 24, 1992 [GB] United Kingdom ............... 9224600
Aug. 13, 1993 [GB] United Kingdom ............... 9316885

[51] Int. Cl.$^6$ ............................................. A61L 9/00
[52] U.S. Cl. ....................................... 239/34; 428/905
[58] Field of Search ................ 428/905; 239/34, 53, 239/54, 60

[56] References Cited

U.S. PATENT DOCUMENTS

| | | | |
|---|---|---|---|
| 3,120,345 | 1/1963 | Bolger | 239/52 |
| 3,261,746 | 12/1962 | Copley | 239/54 X |
| 3,567,119 | 3/1971 | Wilbert et al. | 239/6 |
| 3,685,734 | 8/1972 | Paciorek et al. | 239/54 X |
| 3,688,985 | 9/1972 | Engel | 239/54 |
| 3,876,762 | 4/1975 | Rabussier et al. | 239/60 X |
| 3,910,410 | 10/1975 | Shaw | 206/363 |
| 4,128,508 | 12/1978 | Munden | 512/1 |
| 4,475,663 | 10/1984 | Kittscher et al. | 220/87.1 |
| 4,515,909 | 5/1985 | Sawano et al. | 428/905 X |
| 4,534,509 | 8/1985 | Holzner | 239/34 |
| 4,678,684 | 7/1987 | Sand | 427/213.36 |
| 4,717,017 | 1/1988 | Sprinkel, Jr. et al. | 428/905 X |
| 4,720,409 | 1/1988 | Spector | 239/54 X |
| 4,752,496 | 6/1988 | Fellows et al. | 428/905 X |
| 4,808,454 | 2/1989 | Saitoh | 428/905 X |
| 4,824,707 | 4/1989 | Spector | 428/905 X |
| 4,884,680 | 12/1989 | Israel et al. | 206/44.11 |
| 4,908,252 | 3/1990 | Carnahan et al. | 428/905 X |
| 4,925,517 | 3/1990 | Charbonneau et al. | 428/905 X |
| 4,988,557 | 1/1991 | Charbonneau | 428/905 X |
| 4,990,381 | 2/1991 | Holzner | 428/905 X |
| 5,161,688 | 11/1992 | Muchin | 206/484 |
| 5,249,676 | 10/1993 | Ashcraft et al. | 428/905 X |

FOREIGN PATENT DOCUMENTS

| | | |
|---|---|---|
| 8606499 | 7/1988 | Brazil . |
| 0489205A1 | 6/1992 | European Pat. Off. . |
| 2498903 | of 0000 | France . |
| 1444981 | 8/1976 | United Kingdom ............... 428/905 |
| 2158356 | 11/1985 | United Kingdom . |
| WO92/14607 | 9/1992 | WIPO . |

Primary Examiner—Andres Kashnikow
Assistant Examiner—Lesley D. Morris
Attorney, Agent, or Firm—Charles D. Gunter, Jr.

[57] ABSTRACT

A sampler is shown for a volatile fluid material. The fluid material is applied to a face of a base layer. A cover layer is applied directly over the face without an intermediate layer. A peripheral seal is formed between the base and cover layers. The seal is separable by a user to expose the face of the base layer directly to the atmosphere to allow the fluid volatile material to be released. The cover layer can be replaced to prevent further release of the volatile material. A method is also shown for making the sampler.

14 Claims, 3 Drawing Sheets

PLANAR SAMPLER FOR A LIQUID VOLATILE MATERIAL AND METHOD

Cross-Reference To Related Applications

This application in part discloses and claims subject matter disclosed in the earlier filed pending application Ser. No. 07/922,359, filed Jul. 29, 1992, now U.S. Pat. No. 5,341,992.

The present invention relates to a device, notably to a device for releasing a scent or other volatile material into the environment upon demand.

BACKGROUND TO THE INVENTION

When a person wishes to determine the fragrance of a perfume, deodorant composition or the like, it is conventional to apply a dab or spray of the perfume or other composition onto the wrist of the person, who can then sniff the fragrance at will. However, this then taints the skin of the person for testing the fragrance of another perfume, etc. until the fragrance of the first perfume has dissipated, which may take many minutes. Furthermore, such a method is impractical where the user wishes to take away a sample of the perfume, etc. for assessment by another person at some other location.

It has been proposed to apply the perfume to an absorbent carrier, for example a pad or tissue paper, so as to provide a sample which can be removed by the person for presentation to someone else at a remote location. However, the scent will escape from the pad and this must be enclosed in a fragrance retaining wrapping.

It has been proposed, for example in U.S. Pat. Nos. 4,277,024 and 2,615,754, to apply the perfume or other fragrant composition to a pad which is then sealed in an openable sachet or other purpose-made enclosure to provide a scent sampler, optionally after being retained in position by an apertured layer overlying the pad. The user can then sample the perfume or other volatile material by peeling back the sealing cover to exposed the pad and release the fragrance into the environment. It has also been proposed, see for example U.S. Pat. No. 4,094,119, that the pad is retained in position by a porous intermediate layer through which the volatile material permeates. This intermediate layer regulates the escape of volatile material from the pad.

Such a proposal improves the presentation of the packaged sample so that the sampler can be displayed at the point of sale of the perfume and a prospective purchaser can take a sampler away for assessment by another person at a remote location.

However, the method required to manufacture the sampler is costly, complex and does not readily lend itself to large scale economic production. Thus, the perfume or other material must be applied to a suitable absorbent sheet of carrier material. The sheet must then be cut to form a pad of the desired shape and size and the pad then applied to the desired position on a suitable backing medium. An intermediate perforated cover must then be applied over the pad to secure the pad to the backing sheet while allowing the aroma to escape through the perforations of the cover. Finally, a closure sheet or the like is then applied over the whole to seal in the fragrance and provide a laminated construction from which a disc or the like is then cut to form the sampler unit. Problems are encountered in securing accurate absorption of the material on the carrier, in achieving accurate registration in applying the carrier pad to the backing sheet and in the alignment of the intermediate perforated cover with the pad, and in cutting the required samplers from the resultant composite laminated product.

Since the samplers are to be given away for free at the point of sale or display, any production technique must be as simple and economic as possible. The concept of reducing the problems of accurate registration and cutting in the above proposal by forming a continuous laminated sheet comprising the base layer, a scent impregnated layer, the intermediate layer and the cover layer; and cutting the desired sampler discs from such a composite sheet is unacceptable from a cost and wastage point of view, especially in the case of a sampler for a high quality perfume which may cost many hundreds of dollars per litre where up to half of the applied perfume would be lost in the waste material. Furthermore, it would not overcome the need to apply an adhesive to bond the various layers together and to ensure that the cutting operation cut the composite sheet in register with the adhesive bonding.

It has also been proposed, for example in U.S. Pat. Nos. 3,216,882, 4,874,129 and 4,880,690, to use a gelled absorbent plastic as a matrix within which the perfume is distributed. In such a proposal, the perfume is admixed with the uncured plastic mix and the resultant mixture then set by subjecting the mixture to a curing process involving additional chemicals and/or heating. This process can taint the fragrance and such a proposal has been rejected by the high quality perfume manufacturers on the basis that the product does not give a true rendition of the fragrance.

In place of the absorbent pad or plastic gel matrix, it has been proposed to encapsulate the perfume in a polymer envelope, for example as very small particles—see for example European Patent Applications Nos. 0161091, 0188883 and 0441034 and U.S. Pat. No. 4,720,417. Upon the application of pressure or shear force to the envelope, the envelope ruptures to release the fragrance of the perfume. However, such a proposal again involves the curing of a plastic to form the envelope and this will taint the fragrance of the perfume. Furthermore, where heating is used during the polymer deposition or curing process, this may evaporate the more volatile constituents of the perfume so that some of the highlights of the fragrance of the perfume are lost in the encapsulated sample.

We have now devised a sampler and a method for its manufacture which reduce the above problems and which readily lends itself to cheap large scale economic production.

SUMMARY OF THE INVENTION

Accordingly, the present invention provides a sampler for a volatile fluid material, which sampler comprises:
   a. a vapour barrier base layer having applied directly to a selected area of a first face thereof a volatile fluid material;
   b. a vapour barrier cover layer applied directly and without an intermediate layer over at least said selected area of the said first face of the base layer;
   c. a seal between at least the periphery of said base and cover layers whereby there is formed a vapour barrier enclosure containing said volatile material, said seal being separable whereby a user can separate at least part of said cover layer from said base layer so as to expose at least part of said first face of said base layer directly to the atmosphere and allow the fluid volatile material to be released and to replace said cover layer so as to prevent further release of said volatile material.

From a further aspect, the present invention also provides a method for manufacturing a sampler of the invention, which method comprises:

a. applying a volatile fluid directly to a selected area of a first face of a vapour barrier base layer;
b. applying a vapour barrier cover layer over at least said selected area of said first face of the base layer; and
c. forming a vapour barrier seal between the base and cover layers so as to form with the base and cover layers a vapour barrier enclosure for the volatile material.

Preferably, the volatile material is applied by a roller applicator or an ink jet or other non-contact printing technique.

Surprisingly, we have found that the volatile fluid can be applied directly to the base layer using conventional roller or other printing techniques as if it were a printing ink. Furthermore, we have also found that by suitable selection of the nature of the volatile material and/or its carrier and the nature of the base layer material, the volatile material can be absorbed into the base layer to provide a reservoir of the volatile material so as to achieve a measure of sustained release of the volatile material from the base layer. Thus, it is preferred to apply the volatile material in an alkanol, hydrocarbon or other organic oil carrier to a base layer made from a material which is micro-permeable to the volatile material and/or its carrier. Particularly preferred materials for the base layer are polyesters. The sampler of the invention thus avoids the need for incorporation of the fluid into a porous pad, a polymer gel or into microcapsules as has hitherto been considered necessary. The need for heating or chemical curing of plastics is thus avoided so that the sampler of the invention enables a true rendition of the fragrance of the volatile material to be achieved, which is of special importance in the promotion of high quality perfumes. However, the invention can be applied to a wide range of other materials which readily evaporate at temperatures of up to 37° C., for example medicaments such as natural or synthetic essential oils, for example menthol, eucalyptus, tea tree oil, camphor or lavender oil which, in use, are to be applied to the body of a user and operate by evaporation. The volatile material may also be an insecticide or other volatile biologically active material which it is desired selectively to release into the environment and which is not to be used upon the person. For convenience, the invention will be described hereinafter in terms of the use of a perfume as the volatile material and such perfume can be in the form in which it is applied to the body of a user, typically an oil or an ethanol solution or dilution of such an oil.

Preferably, the volatile material is applied to a substantially central area of a substantially vapour impermeable plastic sheet base layer, which can be in the form of disc, hexagon or the like; the cover layer is provided by a corresponding disc, hexagon or the like of the same or another plastic sheet material. The seal between the base and cover layers can be formed by surface to surface contact adhesion between the opposed faces of the base and cover layers or by an adhesive or other bonding material interface between the opposed faces of the base and cover layers. Preferably, such a seal is formed around the periphery of the contacting opposed faces of the base and cover layers and is conveniently radially inset from the edges of the layers over at least part of its length so as to provide an unbonded tab or edge which can be gripped by the user to separate the base and cover layers when it is desired to release the volatile material into the environment.

The sampler of the invention can be put up in a very simple thin laminate form. Such a laminated structure readily lends itself to large scale production using conventional printing techniques, since the backing and overlay materials are preferably in sheet form and the volatile fluid and any adhesive required to secure the layers together can readily be applied at accurately positioned locations on such sheets by conventional printing techniques. It is no longer necessary to form an intermediate pad which has to be handled and positioned with respect to the backing, thus overcoming the registration problems of prior proposals. The resultant laminated product is slim and can thus be readily applied to the clothes of a user where the sampler is to be used as a source of perfume by the wearer, as well as providing a cheap and readily packaged and displayed means for sampling the perfume at a point of sale. We have found that the perfume can also be readily transferred from the base layer to the skin of a user by wiping the exposed perfume carrying face of the base layer over the skin of a user, so that the sampler can be used to apply substantially consistent amounts of perfume to the wrist, neck or elsewhere of a user.

Furthermore, since the sampler of the invention is both slim and flexible, it readily lends itself to placement upon or between pages of magazines, newspapers and the like where it can advertise a perfume and provide a sample of that perfume which a reader can assess by removing the vapour barrier cover layer. With conventional advertising samplers, the perfume is contained within a plastic encapsulation and/or is incorporated in a wax or hot melt adhesive layer which is located between two opposed pages or sections of a page so that separation of the pages or sections causes release of the perfume. However, the seal between the opposed pages or sections is not good and/or handling of the pages to which encapsulated perfume has been applied often causes premature release of the perfume. Thus, whether a reader wishes it or not, the paper or magazine is tainted with the perfume and the reader is subjected involuntarily to the perfume. This may be unacceptable to many people and may expose them to substances to which they are allergic. The sampler of the invention reduces these problems and provides a means by which a perfume sample can be incorporated into a magazine or the like without exposing the reader to involuntary exposure to the perfume until the cover layer is removed from the sampler to release the perfume.

The invention thus provides two opposed sheets of paper having located between then a sampler of the invention. The sheets of paper may be the pages of a magazine or newspaper or can be the front and back leaves of a greeting or other card.

DESCRIPTION OF THE DRAWINGS

To aid understanding of the invention, it will be described with respect to a preferred form thereof as shown in the accompanying drawings, in which.

DESCRIPTION OF THE PREFERRED EMBODIMENT

Figure 1:
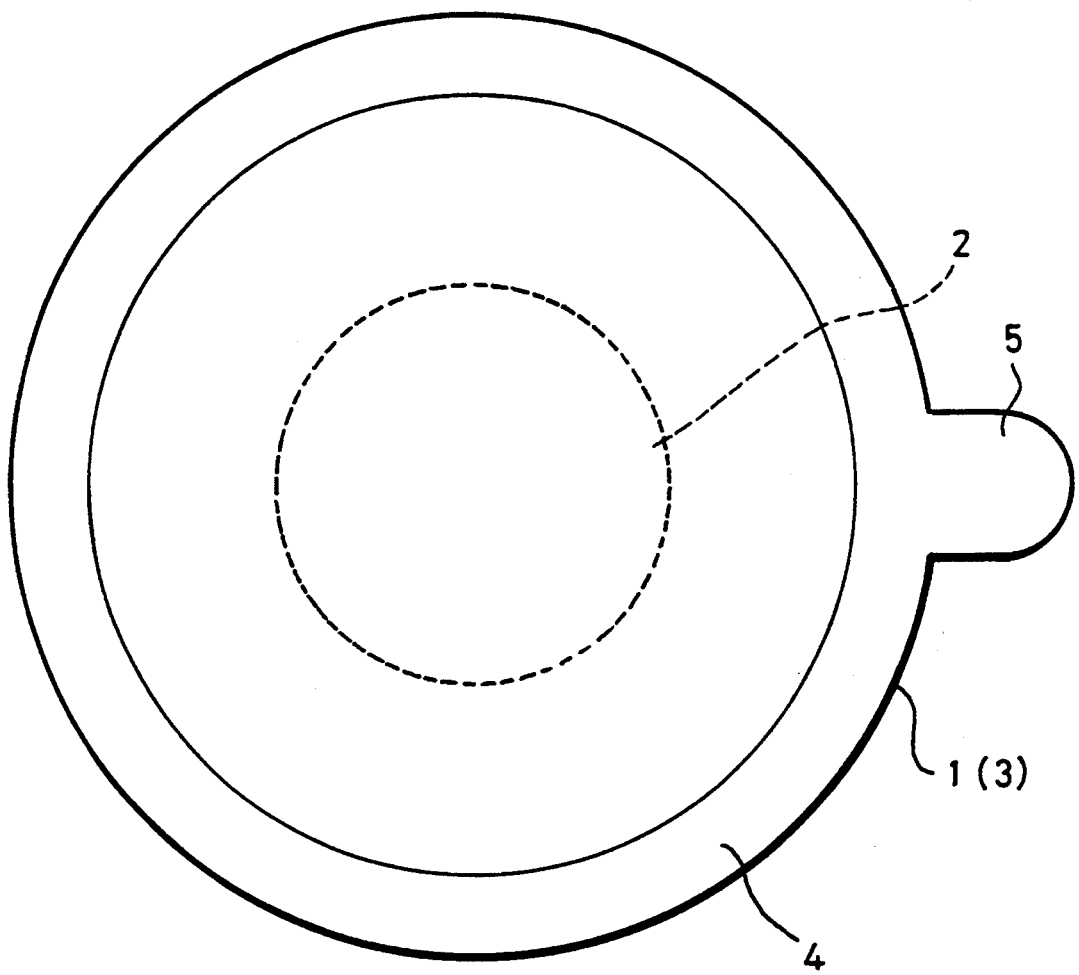
FIG. 1 is a diagrammatic plan view of a disc form of the sampler.
Figure 2:
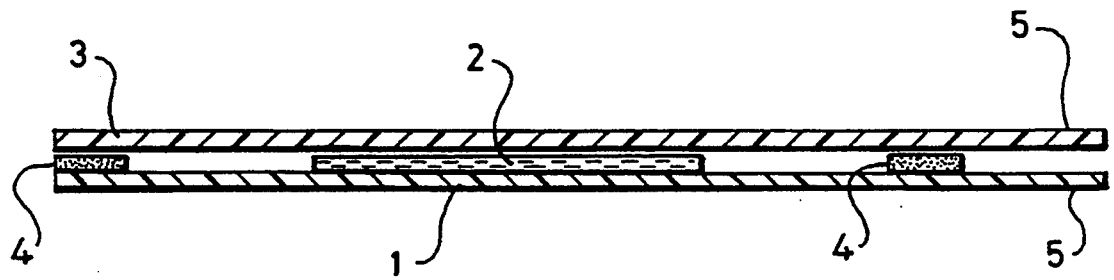
FIG. 2 is a diagrammatic transverse section through the sampler of FIG. 1.
Figure 3:
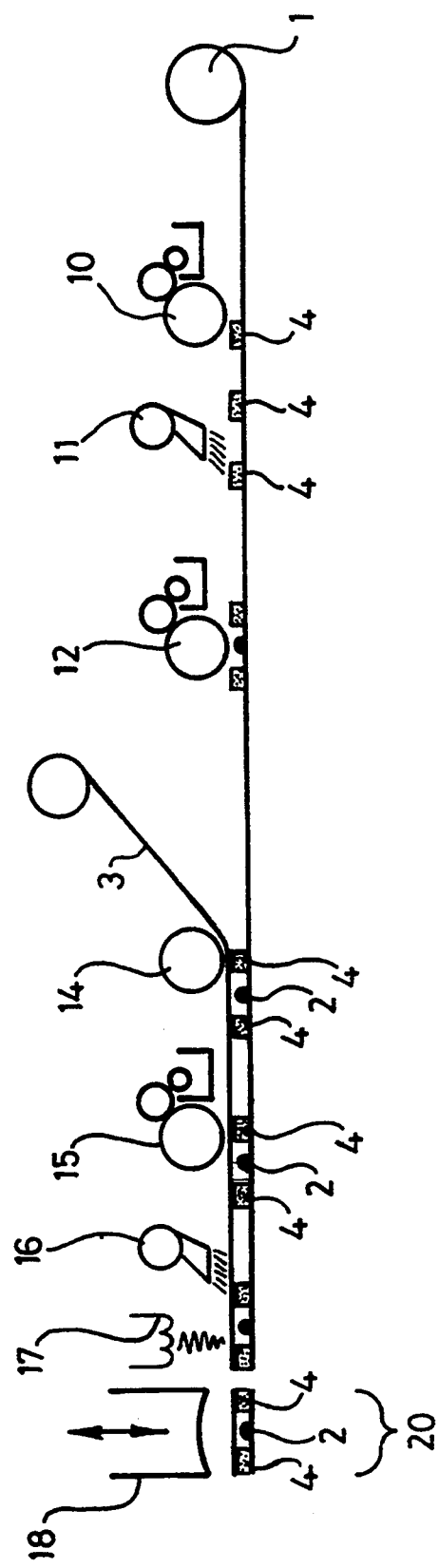
FIG. 3 shows in diagrammatic block form a process for the manufacture of a sampler as shown in FIG. 1.

A sampler according to the invention has the typical structure shown in FIGS. 1 and 2. It comprises a vapour barrier base layer 1 to the upper face of which is applied the desired perfume oil 2 and over which is applied a vapour barrier cover layer 3. In many cases it is necessary to provide a seal ring of adhesive or other bonding agent 4 around the periphery of the base layer 1 to secure the cover layer 3 to the base layer 1. However, in some cases the materials of the base layer 1 and the cover layer 3 can be selected such that their surface energy properties enable then to be auto-adhesive without the need for the adhesive ring 4. The seal may thus extend over substantially the whole of the opposed faces of the base layer 1 and the cover layer 3.

Whilst the sampler is shown in the accompanying drawings as having a substantially circular plan shape, it will be appreciated that the sampler may have any suitable plan shape, e.g. squared, triangular or the complex outline of the shape of a flower whose scent the perfume reproduces. It will also be appreciated that the sampler may be formed into a three dimensional shape, as when the sampler is formed upon or is applied to a scent bottle or the like. For convenience, the invention will be described hereinafter in terms of a generally planar circular plan shaped disc.

The base layer 1 can be made from a wide range of substantially odourless plastic materials which are not degraded or dissolved by the volatile materials to be applied to them and which exhibit adequate vapour barrier properties. Suitable materials for present use include cellulose esters or ethers; acrylate polymers, for example $C_{1-5}$ alkyl esters of $C_{1-5}$ alkylacrylic acids, notably methylmethacrylate polymers; polyesters or polyolefins, notably polyalkylenes such as polyethylenes or polypropylenes; polyurethanes and polyamides.

Preferably, the polymer does not incorporate any significant amount of volatile processing additives such as plasticizers, since these often tend to taint the fragrance of a perfume applied to the polymer sheet. Furthermore, the polymers for present use are preformed, that is they are not used in the form of pre-polymers or oligomers which require thermal and/or chemical curing to achieve the final form in which they are to be present in the sampler, as distinct from the uncured polymer gels which have been used in previous proposals.

Particularly preferred polymers for use in the manufacture of the base layers for present use are those which absorb the perfume or other volatile fluid. This absorbency occurs on a micro scale within a mass of a continuous solid polymer, as opposed to absorbency on a macro scale as occurs when a porous pad, that is a non-continuous solid polymer body, absorbs fluid into the voids or pores within the body. We also believe that the absorbency of the volatile fluid occurs by penetration of the organic molecules of the fragrance and/or its carrier into the solid polymer matrix leading to swelling of the polymer and this provides a prima facie indication that absorbtion of the fluid occurring. Whether a particular polymer is has adequate absorbent properties for use as in this preferred embodiment of the invention is readily determined by suspending the polymer in the volatile fluid which is to be applied to it and determining whether the polymer absorbs sufficient of the fluid at ambient pressure and temperature. Preferably, the polymer absorbs from 0.5 to 5% of its weight of the fluid over a period of 24 hours.

Particularly preferred polymers for use in the base layer are polyester polymers, notably polyethyleneterphthalate polymers. Where laminated materials are used to provide the base layer material, the polyester polymer component of such laminates provides the exposed layer to which the volatile fluid is applied. Thus, the base layer may be a laminate of two or more different materials, for example a polyester top layer with a polyamide and/or polyvinylidenedichloride under layer, bonded together by an adhesive interface, e.g. of a polyacrylic adhesive. If desired, a polyvinylidene-dichloride vapour barrier layer can be incorporated into or applied as an external layer to such laminates.

Accordingly, from a further aspect the present invention provides a sampler for a volatile fluid material, which sampler comprises:

a. a pre-formed polymer base layer having vapour barrier properties, the polymer being selected from polymers which are micro-permeable to organic fluids whereby the polymer absorbs organic fluid applied to a surface thereof and releases the volatile material by volatilization from that surface;

b. an organic volatile fluid material applied directly to a selected area of a first face of the base layer and at least partly absorbed by said base layer whereby the base layer acts as a reservoir from which the volatile fluid may volatilize when exposed to the atmosphere;

c. a cover layer applied over at least said selected area of the said first face of the base layer, the cover layer having vapour barrier properties; and d. means located at least radially outwardly of the said area on the base layer for removably securing the cover layer to the base layer in sealing engagement therewith and thereby form a vapour barrier enclosure around the volatile material whereby the cover layer can be separated at least in part from the base layer to expose at least part of said first face of said base layer directly to the atmosphere.

The invention also provides a method for manufacturing such a sampler, which method comprises:

a. applying a volatile fluid directly to a selected area of a first face of a base layer to form a film or coating of the volatile material on said first face, said first face being provided as a substantially continuous solid form of a polymer which absorbs the volatile fluid;

b. applying a vapour barrier cover layer over at least said selected area of said first face of the base layer; and c. releasably securing the cover layer upon the base layer by a sealing means so as to form with said base layer and the cover layer a vapour barrier enclosure encasing the volatile material.

In order to enhance the adhesion of the perfume and any adhesive to the surface of the polymer of the base layer material, it is preferred to subject the base layer material to corona discharge or other treatment using conventional techniques. For example, the face of the base layer to which the perfume is to be applied can have had a coating of a polyacrylate polymer or other polar material applied thereto as is known in the printing field to aid adhesion of ink to a polymeric substrate.

The base layer may also carry on the reverse face to that to which the perfume is applied an adhesive layer or other means by which the base layer can be secured to the location at which the sampler is to be used. Thus, for example, the base layer can carry a pressure sensitive adhesive layer which is protected during handling and storage by a siliconized paper cover as is conventional in the self-adhesive label art.

The cover layer 3 can be made from the same material as the base layer 1. However, it may be preferred to form the cover layer from a sheet material which autoadheres to the base layer, for example from a polyvinylidenedichloride film such as that known as a cling film, so that the cover layer can be retained on the base layer 1 without the need for an adhesive. Again, it may be preferred to give the cover layer a surface treatment, notably a corona discharge treatment or a polyacrylate or other polar material coating, to aid adhesion of any adhesive or printing thereto.

The perfume is applied directly to the base layer in fluid form and preferably comprises the appropriate perfume oil dissolved in ethanol, water or other substantially odourless solvent or carrier. As indicated above, the perfume can be put up in an oil based carrier as is conventional in the perfume art and we have found that the use of such carriers may assist absorption of the perfume into the base layer and enable a measure of sustained release of the volatile material from the base layer to be achieved. If desired, such an oil based composition can be diluted with ethanol to achieve a desired viscosity for use in the printing technique used to apply the perfume to the base layer 1.

The amount of perfume which is applied to the base layer can vary over a wide range having regard to the strength of the aroma desired and the ability of the base layer and cover layer materials to absorb the perfume and/or its solvent or carrier medium. Preferably, the perfume or other fluid is applied in an amount which is retained upon the base layer by surface tension effects so that the base layer may be handled immediately after the fluid has been applied.

It will be appreciated that, where the preferred micropermeable polymers are used for the base layer, such a surface film or coating of the fluid will progressively be absorbed into the base layer over a period of time to give a substantially dry product. It may therefore be desired to allow a period for absorption of the fluid before the base layer is subjected to further treatment. However, we have found that by suitable selection of the polymer for the base layer and the nature of the fluid, it is practical to handle the base layer directly after application of the fluid and that the absorption of the fluid by the base layer may occur during storage of the completed sampler.

The optimal combination of perfume carrier and polymer for the base layer can readily be established by simple trial and error tests. However, we have found that polyester polymers are surprisingly effective in absorbing many oil based perfumes, typically absorbing from 0.5 to 5% by weight of the perfume applied to it over a period of 24 hours when a sample of the polymer is suspended in the perfume to be applied to it, and do not taint the fragrance of the perfume.

As indicated above, the base layer and cover layer materials may be auto-adherent, whereby they adhere to one another and form a vapour barrier seal around the area to which the perfume has been applied. However, where this is not the case, it is necessary to apply an adhesive or similar bonding agent around the area to which the perfume has been applied to the base layer 1 so as to form a vapour barrier seal around that area and to secure the cover layer 3 upon the base layer 1. As indicated above, the adhesive can be applied over the whole of the opposed faces of the base and cover layers. However, it is preferred to form the seal as an annulus of adhesive 4 around the area to which the perfume has been applied to the base layer. It is also preferred to provide at least part of the radially outward edge of the sampler as an unbonded edge or tab 5 so that a user can more readily roll or peel back one layer from another at that area and thus facilitate separation of the layers.

The adhesive used to bond the two layers together can be a water or solvent based adhesive, for example a pressure sensitive adhesive, e.g. a polyacrylate adhesive, or can be a hot melt adhesive. Where it is necessary to remove water or solvent from the adhesive, it is preferred that this be done before the perfume is applied so as to reduce the risk of tainting the perfume or of removing highlights from the perfume by heating. Alternatively, the adhesive can be one which is cured under UV radiation. The use of water based acrylic polymer adhesives is especially preferred.

The sampler of the invention may comprise merely the above layers of material and the perfume and adhesive. However, it will usually be desired to apply some form of printing to the sampler, for example to print a logo or trade mark on the base layer 1 and/or cover layer 3 to identify the perfume carried by the sampler to a user, notably to print the sampler so that it merges with the page of a magazine or fly sheet to which it is to be applied. Such printing can be achieved using any suitable ink and can be carried out before the base and/or cover layer sheet materials are used to form the sampler. However, in order to reduce tainting of the perfume and loss of highlights due to heating, it is preferred to use UV cured inks, for example dyestuffs with an acrylate polymer binder in an aqueous carrier. The ink can be applied in a separate printing operation from the perfume, and this may be done before or after the application of the perfume to the base layer, for example the ink car be used to overprint the area to which the perfume has been applied. Where the ink is applied over the perfume, the ink may act as a sustained release coating over the perfume. However, it may be desired to apply the ink and perfume simultaneously, for example in admixture with one another, in which case the alcohol or oil carrier for the perfume may also act as the carrier or solvent for the dyestuff used to provide the visual component of such a mixture.

The sampler of the invention is preferably made by applying an adhesive ring 4 around that area 2 of the base sheet 1 to which a perfume is to be applied in a subsequent step and then applying the cover layer 3 over the perfumed area 2 of the base sheet to form a composite laminate from which the required sampler discs are cut by stamping of other techniques. Since the base and cover layer materials are sheet materials, they can be handled at high linear speeds of travel using conventional roller or screen printing machinery with little or no problem in registration between areas of the sheets.

Figure 4:
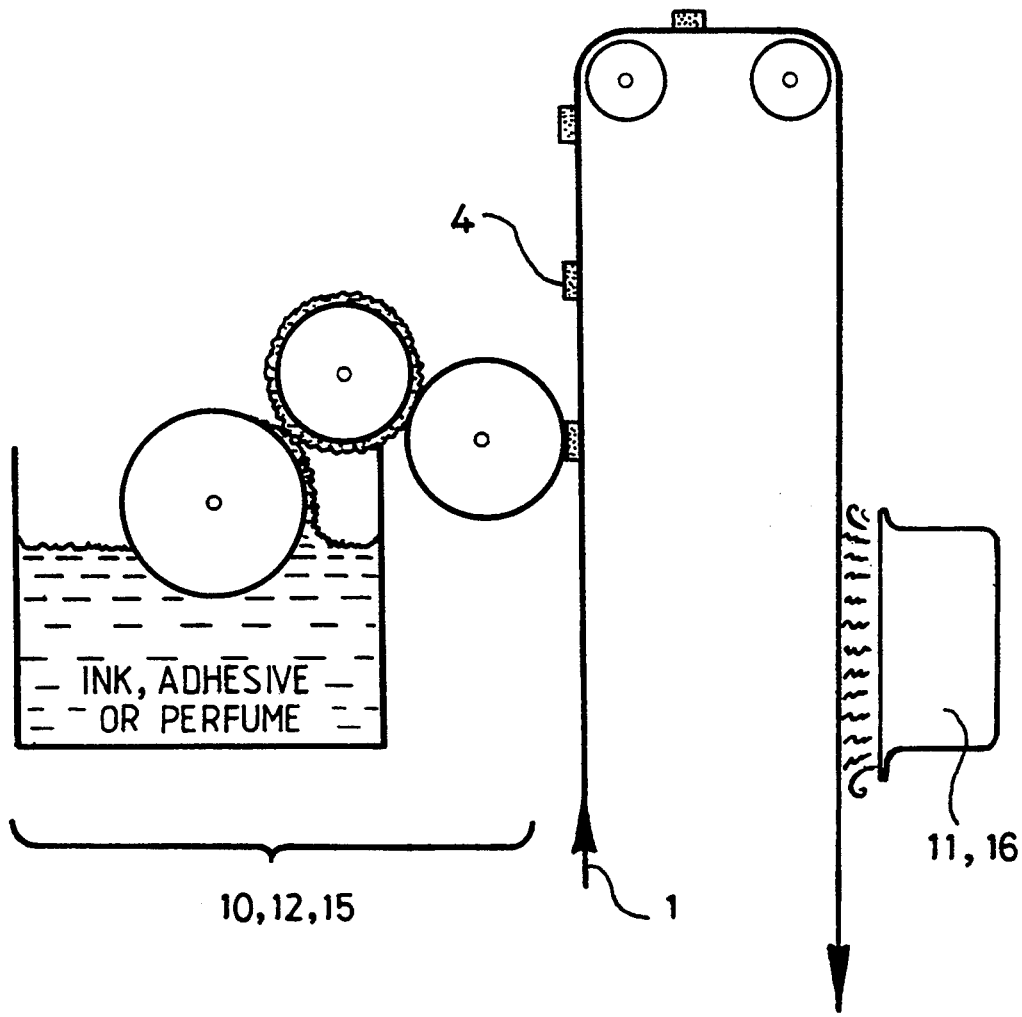
FIG. 4 shows in diagrammatic form a roller applicator for use in the process shown in FIG. 3.

The adhesive is preferably applied to base layer 1 using a conventional sculptured roller applicator 10 of the type shown in FIG. 4. If desired, the adhesive may be dried by a hot air blower 11 before the perfume is applied, notably where the adhesive is a water based composition. Where an image is to be applied to the base layer, this can have been pre-printed onto the base layer material 1 or it can be applied using a conventional screen, roller or ink jet printer either before or after the application of the adhesive and/or the perfume. Again, where the ink is to be dried, this is preferably done using a hot air blower before the perfume is applied.

The perfume is preferably applied by a roller applicator 12, for example one as shown in FIG. 4, after the application and drying of any adhesive or ink compositions. Alternatively, the perfume can be applied by a non contact or ink jet printer technique which can rapidly adjust to alterations in the location of the area 2 to which the perfume is to be applied. The adhesive 4 can be applied by a similar non-contact printing technique, thus also reducing problems in ensuring accurate registration between the perfume application and the base layer material.

The base layer 1 to which the adhesive and perfume have been applied then has the cover layer 3 applied thereto, for example by passing the two layers 1 and 3 carrying the adhesive 4 and the perfume 2 through the nip of a pressure roller 14. Further images can be printed on the outer face of the cover layer 3 using roller or other printing means 15. If desired, the laminated materials can be heated or dried by a hot air blower 16 or other means to remove residual water and/or the ink and/or adhesive can be cured by means of a UV source 17.

The sampler disc 20 is separated from the composite sheet by a stamp or air blade cutter 18 which can form a lobe or other radial extension to part of the rim of the sampler so as to provide a pair of un-bonded tabs 5 which can be used to assist separation of the cover layer 3 from the base layer 1.

The operation of the various stages in building up the composite sampler disc product can be synchronised by any suitable means, for example by applying index markings to the sheets 1 and 3 and providing the printers 10 and 12 and the cutter 18 with means for scanning or detecting these index markings.

The manufacture of the sampler can thus be carried out using conventional high speed printing machines and techniques with reduced risk of mis-alignment of the perfume and the base and cover layers to produce a slim flexible disc or the like.

In a typical operation of the method of the invention, a water based polyacrylic adhesive sold under the trade mark Sericol Drystick or a similar adhesive was applied by a roller applicator to form a ring of adhesive on a Mylar polyester backing sheet 1. In some cases the Mylar was laminated with a polyethylene sheet using a polyacrylate adhesive and the adhesive ring formed on the polyester top layer of such a laminate. The exposed top surface of the polyester sheet had been sprayed with a polar copolymer as conventionally used in the printing industry to improve adhesion of the adhesive ring thereto. The adhesive ring on the sheet was then air dried using a warm air blower.

A perfume oil (18% solution in ethanol) was then applied to the same face of the polyester base sheet within the ring 4 of adhesive using a roller applicator to form a film of perfume which was absorbed into the polyester base sheet to give a dry film upon the base sheet. A cover layer 3 of Polykote polyester sheet was applied over the surface of the base sheet 1 and secured in position by passing the composite material through the nip of a pair of rollers. The sampler discs were cut from the resultant laminate by a roller cutter and stored in a stack before use. This allowed the absorption of the perfume into the base layer 1 to stabilise and thus provide a measure of sustained release once the cover layer 3 was removed.

The above discs retained the fragrance of the perfume until the cover layer 3 was peeled back to allow the perfume to escape into the environment. The cover layer 3 could be spread back over the backing sheet 1 to re-form the vapour barrier seal and thus prevent further release of the perfume.

The samplers of the invention find widespread use wherever it is desired to provide a sealed sample of the perfume which can be opened at will by the user to release the perfume for assessment or enjoyment by the user. Since the perfume is not released until the cover layer is removed, thus breaking the seal between the base and cover layers around the perfumed area of the base layer, a user is not exposed to the perfume until he or she requires it. Similarly, the sampler can be inserted into a magazine or paper to advertise a perfume and a reader of the magazine or paper is not exposed to the perfume unless and until he or she chooses, thus overcoming the problem of involuntary exposure which is inherent with present techniques for presenting scented advertisements to a reader. It will be appreciated in such cases that the base layer may be the one which is removed from the cover layer, depending upon which layer is adhered to the page of the magazine.

The invention has been described above in terms of the base layer carrying a perfume. However, the base layer can carry a wide range of alternative room temperature volatile materials, for example a medicament such as eucalyptus or camphor oil or an insecticide, in which case organic carriers such as cyclohexane or benzene which would not be acceptable for use with perfumes may be used. Similarly, the perfume or other volatile material can be applied to the cover layer described above rather than to the base layer, notably where the base layer carries an adhesive backing whereby it is to be secured to a magazine page or other support.

Since the perfume is applied directly to the base layer and not to an intermediate pad or absorbed into a polymer matrix, the sampler of the invention is of very simple and economic construction. Yet because it does not utilise heating or curing of polymers to contain the perfume, it can be applied to high quality perfumes without significant loss or tainting of the essential flavours a discerning user would otherwise detect.

We claim:
1. A generally planar sampler for a liquid volatile material, which sampler comprises:
   a. a planar substantially vapour proof barrier base layer having applied directly to a selected area of a first face thereof a fluid material containing a liquid volatile material;
   b. a planar substantially vapour proof barrier cover layer applied directly and without an intermediate layer over at least said selected area of said first face of the base layer;
   c. a seal between at least the periphery of said base and cover layers whereby there is formed a sub- stantially vapour proof enclosure for said volatile material, said seal being separable whereby a user can separate at least part of said cover layer from said base layer so as to expose at least part of said first face of said base layer directly to the atmosphere and allow the liquid volatile material to be released by volatilization from said base layer, said seal also being reformable upon replacement of said cover layer so as to prevent further release of said volatile material.

2. A method for manufacturing a sampler which method comprises:
   a. applying a fluid material containing a liquid volatile material directly to a selected area of a first face of a substantially vapour proof barrier base layer;
   b. applying a substantially vapour proof barrier cover layer over at least said selected area of said first face of the base layer; and
   c. forming a substantially vapour proof barrier seal between the base and cover layers so as to form with the base and cover layers a substantially vapour proof enclosure for the liquid volatile material, said seal being separable whereby a user can separate at least part of said cover layer from said base layer so as to expose at least part of said first face of said base layer directly to the atmosphere and allow the liquid volatile material to be released by volatilization from said base layer, said seal also being reformable upon replacement of said cover layer so as to prevent further release of said volatile material.

3. A method as claimed in claim 2, wherein said first face of the base layer comprises a polymer which is micropermeable to the liquid volatile material.

4. A method as claimed in claim 3, wherein said first face of the base layer comprises a polyester polymer.

5. A method as claimed in claim 4, wherein the cover layer is made from a polyester polymer.

6. A method as claimed in claim 2, wherein the liquid volatile material is a perfume.

7. A method as claimed in claim 6, wherein the liquid volatile material is applied in a carrier which assists absorbtion of the liquid volatile material by the base layer.

8. A method as claimed in claim 7, wherein the liquid volatile material is applied to the cover layer.

9. A sampler for a liquid volatile material, which sampler comprises:
   a. a pre-formed polymer base layer having substantially vapour proof barrier properties, the polymer being selected from polymers which are micropermeable to organic fluids whereby the polymer absorbs volatile organic fluid applied to a surface thereof and is capable of releasing the absorbed volatile organic fluid by volatilization from that surface;
   b. a fluid organic material containing a liquid volatile material applied directly to a selected area of a first face of the base layer and at least partly absorbed by said base layer whereby the base layer acts as a reservoir from which the liquid volatile material may volatilize when exposed to the atmosphere;
   c. a cover layer applied over at least said selected area of the said first face of the base layer, the cover layer having substantially vapour proof barrier properties; and
   d. seal means located at least radially outwardly of the said area on the base layer for removably securing the cover layer to the base layer in sealing engagement therewith and thereby form a substantially vapour proof enclosure for said liquid volatile material, said seal means being separable whereby a user can separate said cover layer at least in part from the base layer to expose at least part of said first face of said base layer directly to the atmosphere to allow the liquid volatile material to be released from said base layer.

10. A method for manufacturing a sampler which method comprises:
    a. applying a fluid organic material containing a liquid volatile material directly to a selected area of a first face of a base layer having substantially vapour proof barrier properties to form a film or coating of the liquid volatile material on said first face, said first face being provided as a substantially continuous solid form of a polymer which absorbs the volatile liquid;
    b. applying a substantially vapour proof barrier cover layer over at least said selected area of said first face of the base layer; and
    c. securing the cover layer upon the base layer by a sealing means so as to form with said base layer and the cover layer a substantially vapour proof enclosure for said liquid volatile material, said sealing means being separable whereby a user can separate said cover layer at least in part from the base layer to expose at least part of said first face of said base layer directly to the atmosphere to allow the liquid volatile material to be released from said base layer.

11. The method as claimed in claim 10, wherein the sealing means comprises an adhesive annulus between the opposed faces of the base and cover layers.

12. The method as claimed in claim 10, wherein the adhesive is a water based acrylic polymer adhesive.

13. The method as claimed in claim 10, wherein the base layer comprises a laminate of polymeric sheet materials, said laminate having an exposed face which comprises a polyester polymer.

14. The method as claimed in claim 10, wherein the fluid containing the liquid volatile material is applied by a roller applicator.

* * * * *

UNITED STATES PATENT AND TRADEMARK OFFICE
CERTIFICATE OF CORRECTION

PATENT NO. : 5,439,172
DATED : August 8, 1995
INVENTOR(S) : John Comyn et al.

It is certified that error appears in the above-indentified patent and that said Letters Patent is hereby corrected as shown below:

On the title page, insert item [63] before the heading "Foreign Application Priority Data" please insert the following:

Related U.S. Application Data

Continuation-in-part of Ser. No. 07/922,359, filed Jul. 29, 1992, now U.S. Patent No. 5,341,992.

Signed and Sealed this

Sixteenth Day of July, 1996

Attest:

BRUCE LEHMAN

Attesting Officer

Commissioner of Patents and Trademarks